United States Patent [19]

Nathans et al.

[11] Patent Number: 4,841,024
[45] Date of Patent: Jun. 20, 1989

[54] PURIFICATION OF ANTIBODIES

[75] Inventors: Gene R. Nathans, Columbia; Robert W. Rosenstein, Ellicott City, both of Md.

[73] Assignee: Becton Dickinson and Company, Franklin Lakes, N.J.

[21] Appl. No.: 907,404

[22] Filed: Sep. 15, 1986

[51] Int. Cl.$^4$ ............................................. C07R 3/12
[52] U.S. Cl. ................................... 530/387; 530/413; 530/417; 530/412; 424/85.8; 435/803
[58] Field of Search ............... 530/387, 412, 413, 417; 435/803; 424/85, 85.8

[56] References Cited

U.S. PATENT DOCUMENTS

| | | | |
|---|---|---|---|
| 4,233,286 | 11/1980 | Soothill et al. | 424/84 |
| 4,272,506 | 6/1981 | Schwarzberg | 424/88 |
| 4,560,504 | 12/1985 | Arnold | 424/85 |
| 4,618,589 | 10/1986 | Jifferie et al. | 435/68 |
| 4,639,513 | 1/1987 | Hou et al. | 530/387 |

FOREIGN PATENT DOCUMENTS 0143413  6/1985  European Pat. Off. ............ 530/387

Primary Examiner—Howard E. Schain
Assistant Examiner—Garnette D. Draper
Attorney, Agent, or Firm—Elliot M. Olstein; Raymond J. Lillie

[57] ABSTRACT

I(g)G3 antibody is purified by affinity chromatography and collection of released antibody at a pH of 9.0 to 9.6. The purification is effected in a column containing both an affinity matrix and a desalting matrix, with the column being equilibrated to a pH of from 9.0 to 9.6. I(g)G3 antibody may be stored at pH 9.0 to 9.6.

8 Claims, 1 Drawing Sheet

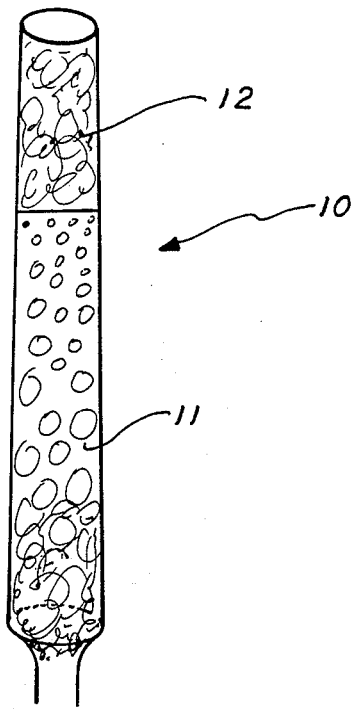

PURIFICATION OF ANTIBODIES

This invention relates to antibodies, and more particularly to the purification of antibodies. Still more particularly, this invention relates to the purification and storage of antibodies of subclass I(g)G3.

Various methods have been previously employed for purification of antibodies. For example, antibodies have been purified by antigen affinity chromatography or protein A affinity chromatography. In attempting to purify antibodies of subclass I(g)G3, difficulties have been encountered in that in such methods the I(g)G3 antibody often precipitates from solution, with such precipitates generally becoming irreversibly insoluble thereby causing loss of purified antibody.

The present invention is directed to improving the purification and storage of antibodies, and in particular, antibodies of subclass I(g)G3.

In accordance with one aspect of the present invention, antibody of subclass I(g)G3 is purified by contacting an affinity matrix with a liquid containing I(g)G3 antibody, with such contacting being effected at a pH of from 9.0 to 9.6 to bind I(g)G3 antibody on the matrix. Subsequently, I(g)G3 antibody is released from the matrix, with the I(g)G3 being collected in a liquid buffered to a pH of from 9.0 to 9.6, and most generally at a pH of approximately 9.3. The antibody is released from the affinity matrix by use of a releasing agent and the I(g)G3 antibody is immediately separated from the releasing agent and collected in an aqueous buffer which is at a pH of from 9.0 to 9.6.

In accordance with a particularly preferred embodiment, the affinity matrix is employed in a column, with the column also containing a desalting matrix, with the affinity matrix being positioned at a point in the column which is above the desalting matrix or gel. In this manner, the released antibody passes into the desalting matrix or gel wherein the releasing agent is separated from the I(g)G3 antibody.

The column is equilibrated to a pH of from 9.0 to 9.6, whereby during the purification, the antibody is maintained at this pH and contact between the antibody and the releasing agent is minimized.

Thus, in accordance with another aspect of the present invention, there is provided a column for purifying antibodies of subclass I(g)G3, wherein the column contains both an affinity matrix and a desalting matrix or gel, with the affinity matrix being placed in the column above the desalting gel, with the entire column being equilibrate to a pH of from 9.0 to 9.6, and most generally a pH of about 9.3.

The antibody of subclass I(g)G3 which is purified in accordance with the present invention may be present as part of a polyclonal antibody or, in accordance with a preferred aspect of the present invention, the antibody which is purified is a monoclonal antibody of subclass I(g)G3. Thus, if the antibody is a polyclonal antibody, the antibody which is purified may contain antibodies other than I(g)G3 antibody and/or may contain more than one antibody of subclass I(g)G3.

The antibody of subclass I(g)G3 which is purified in accordance with the present invention may be obtained by any one of a wide variety of procedures and may be any one of a wide variety of antibodies. As hereinabove indicated, the I(g)G3 antibody is preferably a monoclonal antibody. The procedures for preparing monoclonal antibodies are generally known in the art and such antibodies may be purified in accordance with the present invention.

The affinity matrix which is employed is one which is capable of adsorbing I(g)G3 antibody. Thus, for example, the affinity matrix may include protein A; an antigen for the I(g)G3 antibody which is to be purified, or an antibody for the I(g)G3 antibody which is to be purified, in an immobilized form (supported on a solid support, such as, for example, crosslinked dextran). The selection of a suitable affinity matrix for adsorbing I(g)G3 antibody is deemed to be within the scope of those skilled in the art from the teachings herein; accordingly, no further details in this respect are deemed necessary to enable those skilled in the art to practice the present invention.

The desalting matrix or gel which is employed in the present invention is any one of a wide variety of matrices which are suitable for desalting (separation of small salt ions or molecules from larger molecules). Such matrices are often referred to as gels and the procedure employing such matrices is often referred to as gel filtration. In accordance with the present invention, the desalting matrix is employed to provide a separation between I(g)G3 antibody released from the affinity matrix and the material or materials which are used for releasing I(g)G3 antibody from the affinity matrix. As representative examples of such desalting matrices, there may be mentioned: crosslinked dextran (for example, of the type sold under the mark "Sephadex G-25") and polyacrylamide beads (for example, of the type sold under the mark Bio-Rad P-2).

The column may be equilibrated to a pH which is at least 9.0 and which is no greater than 9.6 by use of a wide variety of buffers and the selection of a suitable buffer is deemed to be within the scope of those skilled in the art from the teachings herein. For example, the buffer may be a sodium bicarbonate, a sodium borate or a Tris buffer. A representative buffer is 0.1M sodium borate buffer which provides a pH of about 9.3.

The releasing agent which is employed for releasing antibody from the affinity matrix may be any one of a variety of such releasing agents. In general, such releasing agents are aqueous buffers buffered to a pH of no greater than 4.0. In most cases, the buffer does not have a pH of less than 2.0; however, it is to be understood that a lower pH may be employed. The releasing agent could be a chaotropic agent (for example, sodium or potassium thiocyanate); a denaturant such as guanidine hydrochloride or urea, etc. The selection of a suitable releasing agent is deemed to be within the scope of those skilled in the art from the teachings herein.

As hereinabove indicated, in accordance with the present invention, contact between antibody and the releasing agent is minimized, and during purification by use of an affinity matrix, the antibody is maintained and collected at a pH of no less than about 9.0 and no greater than about 9.6.

BRIEF DESCRIPTION OF THE DRAWINGS

The present invention will be further described with respect to the accompanying drawing, wherein:

The drawing is a schematic diagram of a chromatographic column in accordance with the present invention.

Referring now to the drawing, there is shown a chromatographic column 10, which includes a desalting gel 11, and an affinity gel 12 layered above the desalting gel 11. As hereinabove described, the affinity gel is preferably protein A, and the desalting gel is preferably Sephadex.

The column is generally formed in a manner such that the volume of the desalting matrix 11 is at least two times, and preferably at least four times, the volume of the affinity matrix 12. The difference in volume enhances the rapid separation between the releasing agent and the released antibody in the desalting gel 11.

The column 10 is equilibrated to a pH of at least 9.0 and no greater than 9.6, as hereinabove described.

A sample containing I(g)G3 antibody is introduced into the top of column 10. The sample may be sera, tissue culture media, ascites fluid, etc. The sample preferably contains monoclonal antibody of subclass I(g)G3. The sample may be added as is or may be a clarified supernate.

The antibody is adsorbed on affinity matrix 12 and the column is washed with an aqueous buffer which is at a pH of at least 9.0 and no greater than 9.6.

After washing, a releasing agent is added to the top of Column 10; for example, an aqeuous buffer which is at a pH of no greater than 4.0. The change in pH releases the antibody from the affinity matrix 12, and the released antibody migrates ahead of the releasing agent into the desalting matrix 11 wherein the released antibody, in the aqueous buffer which is at the pre-equilibrated pH of at least 9.0 and no greater than 9.6 is separated from the releasing agent. In this manner, contact between the released antibody and the releasing agent is minimized and the antibody is effectively maintained at a pH of at least 9.0 and no greater than 9.6 during purification on Column 10.

The volume of releasing agent which is added to Column 10 is controlled so as to permit both release of the antibody from the affinity matrix and separation of the released antibody from the releasing agent, while maintaining the antibody at a pH of at least 9.0 and no greater than 9.6. Thus, for example, the releasing agent may be added in a volume which is one to two times the volume of the affinity matrix 12.

Thus, as should be apparent, the relative volumes of the affinity matrix 12, the desalting matrix 11 and the releasing agent added to the column are controlled to provide for separation of released antibody from the releasing agent, and collection of released antibody in an aqueous buffer having a pH of at least 9.0 and no greater than 9.6.

The column may be employed as hereinabove described for purification of I(g)G3 antibody and, in particular, monoclonal antibody of subclass I(g)G3.

In accordance with a further aspect of the present invention, there is provided a composition containing I(g)G3 antibody in an aqueous buffer having a pH of at least about 9.0 and no greater than about 9.6, and most generally a pH of about 9.3. The I(g)G3 antibody may be a monoclonal antibody or may be part of a polyclonal antibody mixture. The use of such an aqueous buffer improves the storage stability of I(g)G3 antibodies.

The invention will be further described with respect to the following example; however, the scope of the invention is not to be limited thereby:

EXAMPLE

A column approximately 1 cm in diameter by 30 cm in length (24 ml volume) was used for the purification of an IgG(3) monoclonal antibody ascites. The column was constructed by first filling it with 19 ml (24 cm) of crosslinked dextran (Sephadex G-25). Protein A supported on crosslinked dextran (Sepharose CL-4B, Sigma P-3391) was swollen in distilled water and approximately 5 ml (6 cm) was layered over the Sephadex G-25. The column was pre-equilibrated with several passages of 0.1M sodium borate (pH 9.3). The ascites mixture was layered on and into the column, and then followed by thorough washing with several column volumes of sodium borate buffer. This removes any residual proteins derived from the ascites. After this wash step, 10 ml of 0.1M sodium citrate (pH 3.5) was layered over the Protein A/Sepharose CL-4B matrix until all sodium citrate buffer passed into the affinity matrix. The 0.1M sodium borate reservoir was reconnected to the column after the sodium citrate buffer passed into the column to elute protein. This step was continued until all the antibody eluted from the column and the column was re-equilibrated with 0.1M sodium borate at pH 9.3. At this point, the column can be used again for antibody purification. The IgG(3) was eluted in fraction 11 while the citrate buffer eluted in fraction 24.

The present invention is particularly advantageous in that it is possible to obtain highly purified antibody in a rapid and reproducible manner, without the problems heretofore encountered with respect to irreversible precipitation of antibody. Moreover, the methodology is amenable to automation on computerized and programmable purification systems. Furthermore, it is now possible to recover and store I(g)G3 antibody without the problems heretofore encountered in the art; e.g., without irreversible precipitation of antibody. These and other advantages should be apparent to those skilled in the art from the teachings herein.

What is claimed is:

1. A process for purifying I(g)G3 antibody, comprising:
    contacting a liquid containing I(g)G3 antibody with an affinity matrix for I(g)G3 antibody which is maintained at a pH of at least 9.0 and no greater than 9.6 to adsorb I(g)G3 antibody; releasing adsorbed I(g)G3 antibody from the affinity matrix; and collecting released I(g)G3 antibody in an eluate which is at a pH of at least 9.0 and no greater than 9.6.

2. The process of claim 1 wherein the adsorbed I(g)G3 antibody is released into a desalting matrix maintained at a pH of at least 9.0 and no greater than 9.6.

3. The process of claim 2 wherein the adsorbed I(g)G3 antibody is released by contacting the affinity matrix with a releasing agent and separating the releasing agent and released I(g)G3 antibody in the desalting matrix.

4. The process of claim 3 wherein the releasing agent is an aqueous buffer having a pH of no greater than 4.0.

5. The process of claim 3 wherein said releasing agent is selected from the class consisting of sodium thiocyanate, potassium thiocyanate, guanidine hydrochloride, and urea.

6. The process of claim 4 wherein the volume of the desalting matrix is at least two times greater than the volume of the affinity matrix.

7. The process of any one of claims 1, 2, 3, 4 or 6 wherein the I(g)G3 antibody is a monoclonal antibody.

8. The process of claim 2 wherein the pH of the desalting matrix, affinity matrix and eluate is about 9.3.

* * * * *